(12) United States Patent
Pryor (10) Patent No.: US 7,635,382 B2
(45) Date of Patent: Dec. 22, 2009

(54) DELIVERY SYSTEM FOR LONG SELF-EXPANDING STENTS

(75) Inventor: Jack D. Pryor, Windsor, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 932 days.

(21) Appl. No.: 10/691,747

(22) Filed: Oct. 22, 2003

(65) Prior Publication Data

US 2005/0090887 A1 Apr. 28, 2005

(51) Int. Cl.
*A61F 2/06* (2006.01)
(52) U.S. Cl. .................................................. 623/1.11
(58) Field of Classification Search ................ 623/1.11, 623/1.12, 1.23, 1.2; 606/108, 181–184, 107, 606/191–198
See application file for complete search history.

(56) References Cited

U.S. PATENT DOCUMENTS

| 5,741,288 | A | * | 4/1998 | Rife | 606/181 |
| 6,113,608 | A | * | 9/2000 | Monroe et al. | 623/1.11 |
| 6,168,606 | B1 | * | 1/2001 | Levin et al. | 606/181 |
| 6,206,888 | B1 | * | 3/2001 | Bicek et al. | 606/108 |
| 6,387,118 | B1 | | 5/2002 | Hanson | 623/1.11 |
| 2006/0142833 | A1 | * | 6/2006 | Von Oepen et al. | 623/1.11 |

* cited by examiner

*Primary Examiner*—Kevin T Truong
(74) *Attorney, Agent, or Firm*—Serge Hodgson (57) ABSTRACT

The initial deployment of a self-expanding stent is performed by the physician manually retracting the sheath of a delivery system. This provides the physician with complete control of the initial deployment of the stent. Further, once the stent is securely engaged within the parent vessel, the remaining deployment over the remaining length of the stent is performed automatically by retraction of the sheath by a spring. Since the physician simply initiates the deployment of the stent, the deployment is readily performed using only a single hand of the physician.

27 Claims, 9 Drawing Sheets

DELIVERY SYSTEM FOR LONG
SELF-EXPANDING STENTS

BACKGROUND OF THE INVENTION

1. Field of the Invention

The present invention relates to an intra-vascular device and method. More particularly, the present invention relates to a device for deployment of a stent for treatment of luminal, i.e., intra-vascular, diseases.

2. Description of the Related Art

In stent deployment systems, a self-expanding stent was restrained within a sheath. After positioning of the stent at the desired location via fluoroscopic guidance, the physician retracted the sheath to deploy the stent, i.e., to expose the stent and allow it to self-expand. To completely deploy the stent, the physician had to retract the sheath over the entire length of the stent, which was relatively cumbersome and typically required the use of both hands or repeated motion of the physician in the case of long self-expanding stents. Other devices required repeated motions such as ratcheting, using a thumbwheel or lever.

SUMMARY OF THE INVENTION

In one embodiment, a method of deploying a stent includes manually retracting a sheath to initiate deployment of the stent, connecting a slider coupled to the sheath to an engagement plate, and disengaging the engagement plate from a housing to allow a spring to retract the engagement plate and thus the sheath to automatically complete deployment of the stent.

The method is well suited for use when the stent is long. More particularly, the initial deployment of the stent is performed by the physician manually. This provides the physician with complete control of the initial deployment of the stent. Further, once the stent is securely engaged within the parent vessel, the remaining deployment over the remaining length of the stent is performed automatically by retraction of the sheath by the spring. Since the physician simply initiates the deployment of the stent, the deployment is readily performed using only a single hand of the physician. Accordingly, relatively long stents are deployed in a very simple manner.

In another embodiment, a delivery system includes: a housing; a sheath; a slider coupled to the sheath, the slider being located within the housing; an engagement plate coupled to the housing; and a source of stored energy coupled to the engagement plate.

The present invention is best understood by reference to the following detailed description when read in conjunction with the accompanying drawings.

BRIEF DESCRIPTION OF THE DRAWINGS

Common reference numerals are used throughout the drawings and detailed description to indicate like elements.

DETAILED DESCRIPTION

A method of deploying a stent 110 (FIG. 1) includes manually retracting a sheath 112, by moving an actuation button 134 on delivery handle 114 that is connected to sheath 112, to initiate deployment of stent 110, connecting a slider 122 coupled to sheath 112 to an engagement plate 126 (FIG. 2), and disengaging engagement plate 126 from a housing 120 (FIG. 3) to allow a spring 128 to retract engagement plate 126 and thus sheath 112 to automatically complete deployment of stent 110.

The method is well suited for use when stent 110 is long. More particularly, the initial deployment of stent 110 (FIGS. 1 and 2) is performed by the physician manually. This provides the physician with complete control of the initial deployment of stent 110. Further, once stent 110 is securely engaged within parent vessel 102, the remaining deployment over the remaining length of stent 110 (FIG. 3) is performed automatically by retraction of sheath 112 by spring 128. For shorter length stents the automatically deployed length could be a short section (length). Since the physician simply initiates the deployment of stent 110, the deployment is readily performed using only a single hand of the physician. Accordingly, relatively long stents are deployed in a very simple manner.

Figure 1:
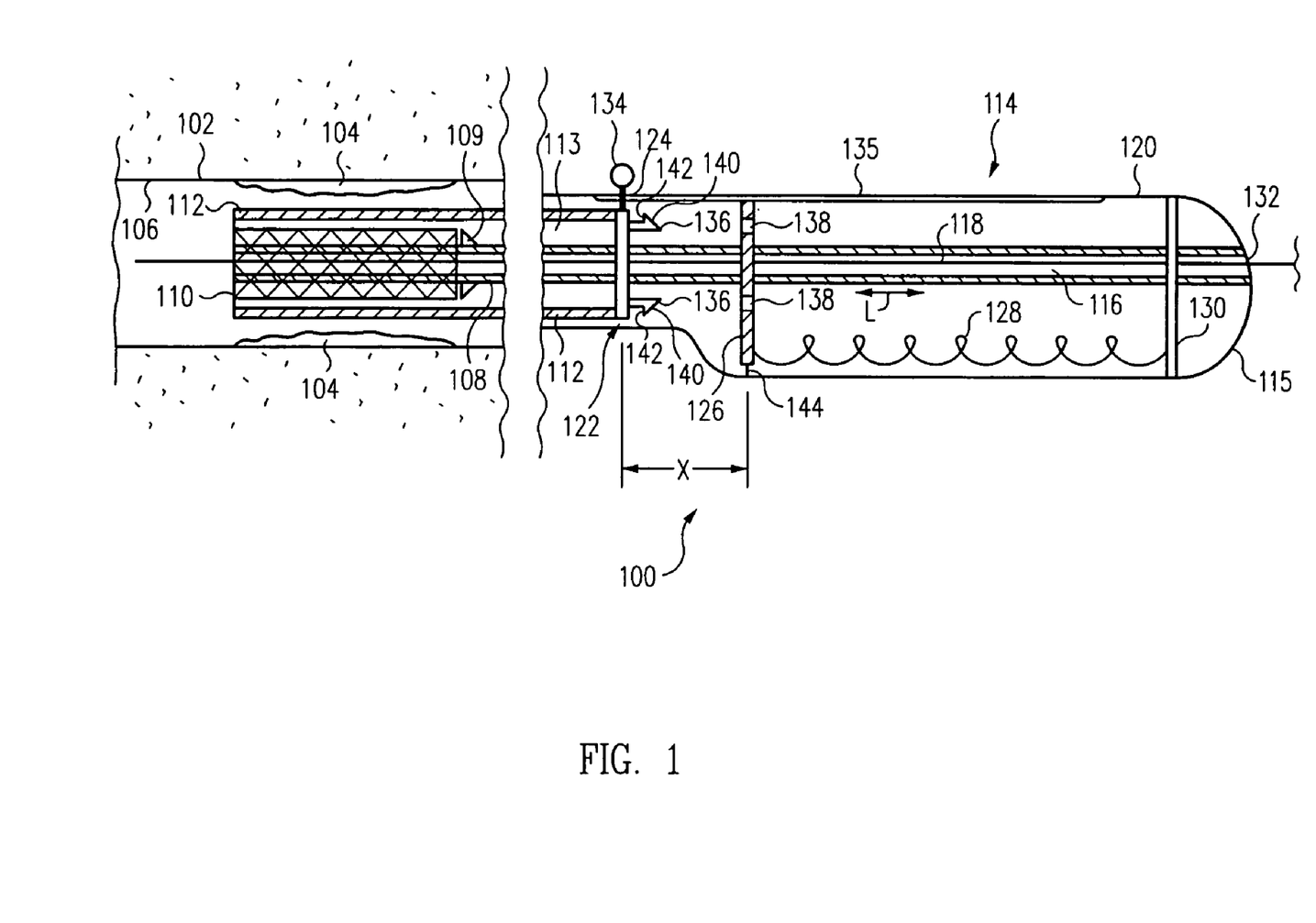
FIG. 1 is a modified partial cross-section view of a stent delivery system within a parent vessel of a patient adjacent to an occlusion.

More particularly, FIG. 1 is a modified partial cross-section view of a stent delivery system 100 within a parent vessel 102 of a patient adjacent to an occlusion 104. Occlusion 104 occludes or completely blocks blood flow through parent vessel 102. Illustratively, occlusion 104 is plaque, thrombi, other deposits, emboli or other substances on an inner vessel wall 106 of parent vessel 102. Occlusion 104 reduces the blood carrying capacity of parent vessel 102. Left untreated, occlusion 106 could cause serious and permanent injury, or even death to the patient.

Delivery system 100 includes an inner member 108, a stent 110, a sheath 112, and a delivery handle 114.

In accordance with this embodiment, inner member 108, sometimes called a pushrod, is a hollow tubular member and includes a lumen 116, e.g., a guidewire lumen, through which a guidewire 118 extends.

Stent 110 is placed over and positioned around inner member 108. In one embodiment, inner member 108 and/or stent 110 include radiopaque markers, which allow the location of stent 110 to be precisely tracked facilitating positioning of stent 110 within parent vessel 102.

Stent 110 is radially constrained by sheath 112. More particularly, prior to deployment, stent 110 is located within sheath 112. Sheath 112 extends into and is coupled to delivery handle 114 as discussed further below. Sheath 112 includes a lumen 113 through which inner member 108 and guidewire 118 extend.

Delivery handle 114 includes a housing 120, a slider 122, a slider movement mechanism 124, an engagement plate 126, a spring 128, and an anchor plate 130. Inner member 108 extends through delivery handle 114 to a guidewire port 132 of housing 120. More particularly, slider 122, engagement plate 126, and anchor plate 130 include apertures through which inner member 108 passes.

Slider 122, sometimes called a traveller, is coupled to slider movement mechanism 124, which is slidably coupled to housing 120. Slider movement mechanism 124, sometimes called a thumb slider, includes an actuation button 134. Slider movement mechanism 124 extends from inside housing 120 through a slider movement mechanism slot 135 of housing 120.

Sheath 112 is coupled to or integral with slider 122. Depression of actuation button 134 (or circumferential rotation) disengages slider movement mechanism 124 from housing 120. This allows slider movement mechanism 124, and thus slider 122 and sheath 112, to be moved longitudinally along a longitudinal axis L of delivery handle 114.

Prior to retraction of sheath 112, a longitudinal manual pull distance X exists between slider 122 and engagement plate 126. Generally, retraction is movement towards a proximal end 115 of delivery handle 114 and anchor plate 130.

Slider 122 and engagement plate 126 include means for connecting slider 122 to engagement plate 126. More particularly, slider 122 includes one or more locking protrusions 136, sometimes called tabs or hooks, extending from slider 122 towards engagement plate 126. Engagement plate 126 includes locking apertures 138 corresponding to and aligned with locking protrusions 136. As discussed further below in reference to FIG. 2, slider 122 is retracted towards engagement plate 126 such that locking protrusions 136 pass through corresponding locking apertures 138 and snap to connect slider 122 to engagement plate 126.

Figure 2:
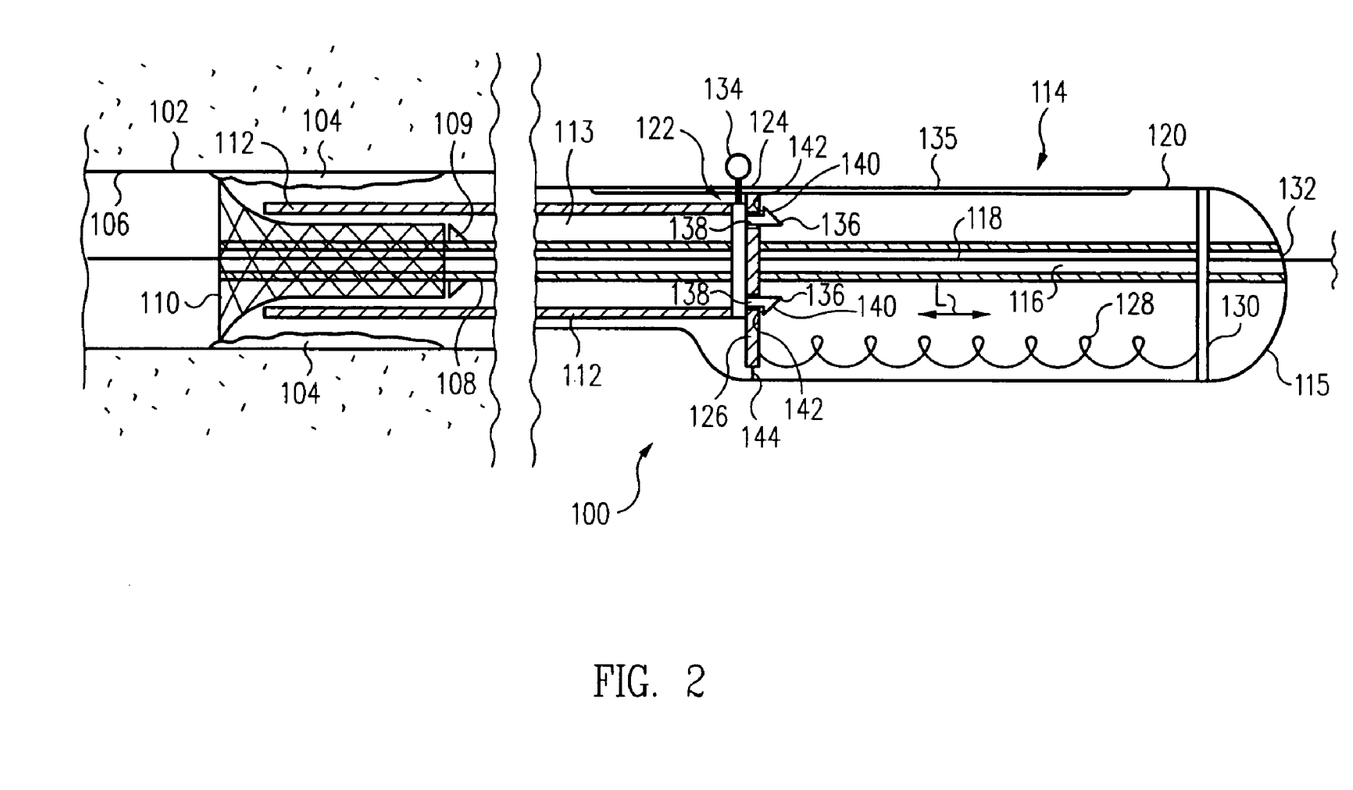
FIG. 2 is a modified partial cross-section view of the stent delivery system of FIG. 1 during deployment of the stent.

FIG. 2 is a modified partial cross-section view of stent delivery system 100 of FIG. 1 during deployment of stent 110. Referring now to FIGS. 1 and 2 together, to deploy stent 110, slider movement mechanism 124 is retracted manually by the physician. Since slider 122 and sheath 112 are coupled to slider movement mechanism 124, retraction of slider movement mechanism 124 causes retraction of sheath 112.

As sheath 112 is retracted, the first portion, e.g., the first few segments and/or the first few millimeters, hereinafter referred to as the first few segments, of stent 110 are uncovered by sheath 112 and exposed. As a result, the first few segments of stent 110 self-expand into occlusion 104 and inner vessel wall 106 of parent vessel 102 thus providing a force opening that part of parent vessel 102 and engaging stent 110 to inner vessel wall 106. Inner member 108 includes a stop 109 or other holding member, which prevents movement of stent 110 during retraction of sheath 112.

These first few segments of stent 110 are deployed manually by the physician. This allows the physician to carefully deploy the first few segments of stent 110 to achieve the desired positioning of stent 110 within parent vessel 102 and occlusion 104. Further, by manually deploying the first few segments of stent 110, the physician is in complete control of the initial positioning of stent 110 and further facilitating the desired positioning of stent 110 within parent vessel 102 and occlusion 104.

After slider movement mechanism 124, slider 122 and sheath 112 are retracted, i.e., moved manual pull distance X, slider 122 contacts and connects to engagement plate 126 as shown in FIG. 2.

More particularly, locking protrusions 136 include tapered surfaces 140, i.e., surfaces angled with respect to longitudinal axis L of delivery handle 114. Tapered surfaces 140 contact the sides of locking apertures 138. Locking protrusions 136 are thus bent as slider 122 is retracted. Locking protrusions 136 further include lips 142, e.g., surfaces perpendicular to longitudinal axis L of delivery handle 114. Once lips 142 of locking protrusions 136 completely passed through locking apertures 138, locking protrusions 136 snap around engagement plate 126 thus connecting slider 122 to engagement plate 126 as shown in FIG. 2.

Further, referring again to FIG. 1, manual pull distance X controls how much length of stent 110 is exposed by sheath 112 prior to engagement of slider 122 to engagement plate 126. Accordingly, by appropriately defining manual pull distance X, a desired length of stent 110 is exposed by manual retraction of sheath 112. Typically, manual pull distance X is sufficient to expose enough length of stent 110 to cause stent 110 to engage inner vessel wall 106 of parent vessel 102.

Referring now to FIG. 2, anchor plate 130 is fixed to or integral with housing 120. Engagement plate 126 is coupled to anchor plate 130 by spring 128. Spring 128 is in tension and is a source of stored energy. Although spring 128 is set forth, other sources of stored energy can be used. Further, it is understood that the figures are not to scale and the ratio of the expanded length to the compressed length of spring 128 can be other than that illustrated.

Engagement plate 126 is coupled to housing 120 by at least one breakaway 144 of delivery handle 114. Breakaways 144 have a strength sufficient to prevent disengagement of engagement plate 126 from housing 120 during coupling of slider 122 to engagement plate 126 as discussed above. However, after engagement of slider 122 to engagement plate 126, additional force applied during the manual retraction of slider movement mechanism 124 causes breakaways 144 to release engagement plate 126 from housing 120 as discussed further below in reference to FIG. 3. In one embodiment, breakaways 144 are thin strips of molding between engagement plate 126 and housing 120 and break or snap to release engagement plate 126 from housing 120.

Figure 3:
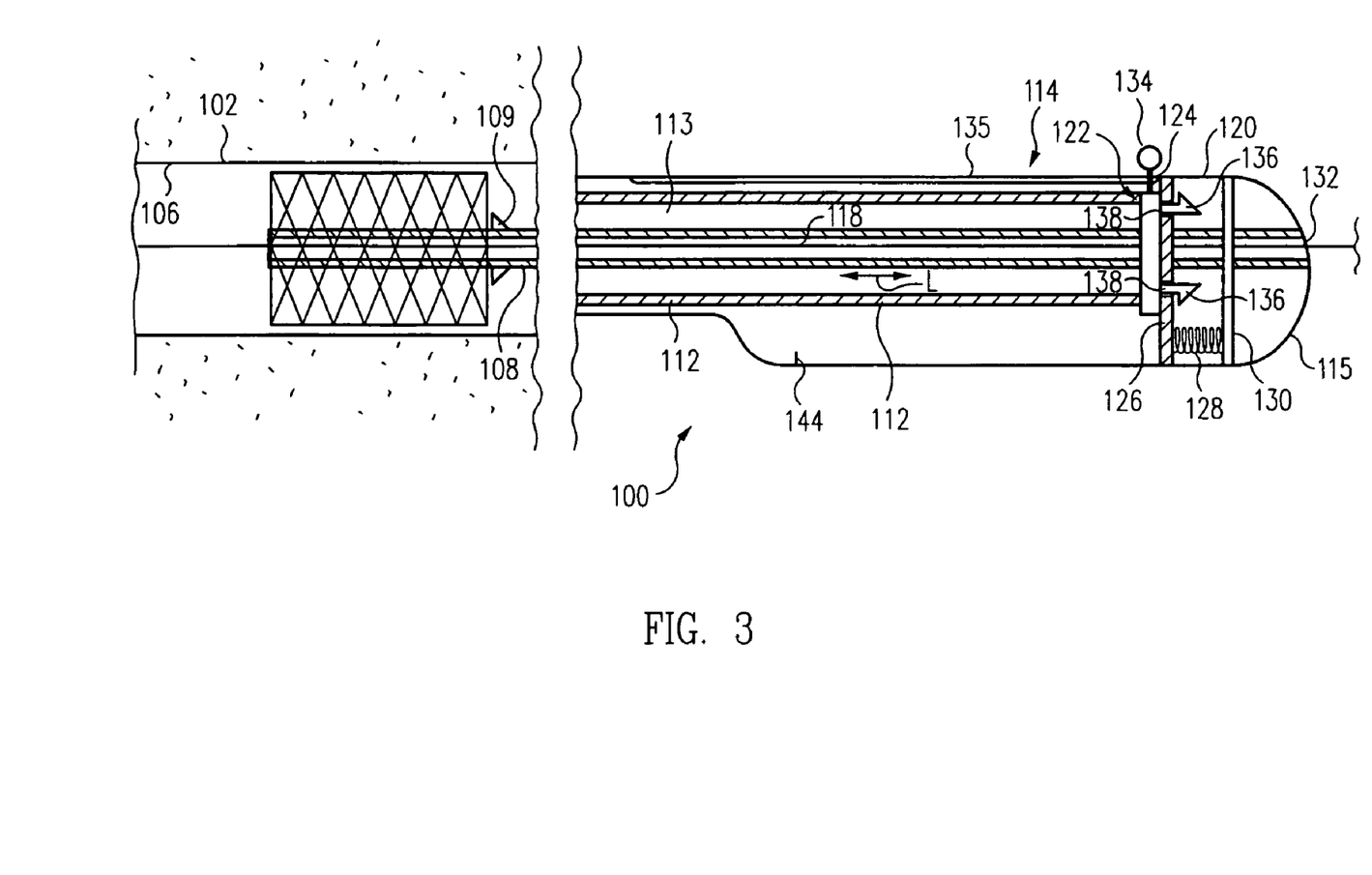
FIG. 3 is a modified partial cross-section view of the stent delivery system of FIG. 2 at a further stage during deployment of the stent.

FIG. 3 is a modified partial cross-section view of stent delivery system 100 of FIG. 2 at a further stage during deployment of stent 110. Referring now to FIGS. 2 and 3 together, upon release by breakaways 144 and disengagement of engagement plate 126 from housing 120, spring 128 moves (pulls) engagement plate 126 towards anchor plate 130, i.e., automatically retracts engagement plate 126. Since slider 122 and sheath 112 are connected to engagement plate 126, slider 122 and sheath 112 are also pulled towards anchor plate 130. This results in automatic retraction of sheath 112 from stent 110, which self-expands to become fully deployed within parent vessel 102 as shown in FIG. 3. Illustratively, friction between engagement plate 126 and housing 120 as discussed below, may control the speed of retraction of sheath 112.

Use of delivery handle 114 is particularly well suited for use when stent 110 is long, e.g., 200 mm or greater, although stent 110 can be less than 200 mm depending upon the application. More particularly, the initial deployment of stent 110 is performed by the physician manually. This provides the physician with complete control of the initial deployment of stent 110. Further, once stent 110 is securely engaged within parent vessel 102, the remaining deployment over the remaining length of stent 110 is performed automatically by retraction of sheath 112 by spring 128 as discussed above. Since the physician simply moves the slider movement mechanism 124 over the relatively short manual pull distance X (FIG. 1), the deployment of stent 110 is readily performed using only a single hand of the physician. Accordingly, use of delivery handle 114 allows deployment of relatively long stents in a very simple manner.

Referring again to FIGS. 2 and 3, during retraction of engagement plate 126 by spring 128, slider movement mechanism 124 travels the length of delivery handle 114. To facilitate this travel of slider movement mechanism 124, slider movement mechanism slot 135 extends along the length of delivery handle 114.

To stop the retraction of engagement plate 126 by spring 128 and automatic deployment of stent 110, the physician simply stops the movement of actuation button 134. To continue the automatic deployment of stent 110, the physician simply releases actuation button 134. Further, if desired, the physician can manually deploy stent 110 by manually moving actuation button 134 across the length of delivery handle 114.

Figure 4:
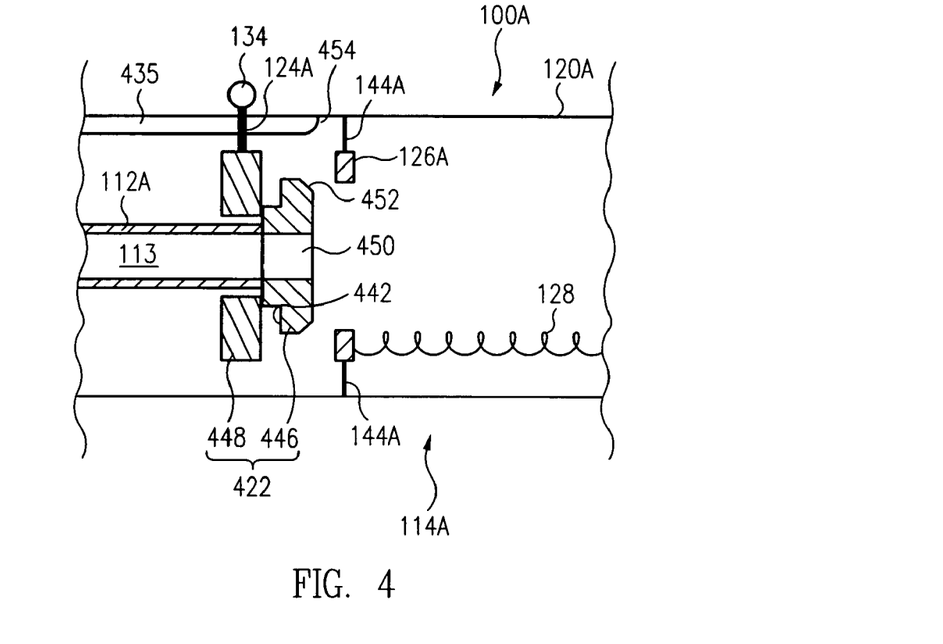
FIG. 4 is a modified partial cross-section view of another stent delivery system.

FIG. 4 is a modified partial cross-section view of a stent delivery system 100A in another embodiment according to the present invention. In FIG. 4, inner member 108 and guidewire 118 (FIGS. 1, 2, and 3) are not illustrated for simplicity.

A slider 422 includes a collet 446, sometimes called an engaging piece, and a collar 448. Sheath 112A is coupled to collet 446. Collet 446 includes an aperture 450 aligned with lumen 113 of sheath 112A, through which inner member 108 passes.

Collar 448 is an annulus slidably mounted around sheath 112A. Collar 448 is coupled to a slider movement mechanism 124A, which is slidably coupled to a housing 120A. Slider movement mechanism 124A include actuation button 134. Slider movement mechanism 124A extends from inside housing 120A through a slider movement mechanism slot 435 of housing 120A.

An engagement plate 126A is an annular shaped member, e.g., an annulus, coupled to housing 120A by one or more breakaways 144A. Spring 128 is coupled to engagement plate 126A in a manner similar to that discussed above with regards to engagement plate 126 (FIGS. 1 and 2).

Collet 446 includes a tapered surface 452 to facilitate coupling of collet 446 to engagement plate 126A. Further, collet 446 includes a lip 442, e.g., an annular surface.

In a manner similar to that described above with reference to FIGS. 1 and 2, slider movement mechanism 124A is manually retracted by the physician to initiate deployment of the stent. Slider movement mechanism 124A is connected to collar 448 and thus retraction of slider movement mechanism 124A causes retraction of collar 448.

Collar 448 is in abutting contact with collet 446 and thus retraction of slider movement mechanism 124A causes retraction of collet 446. Sheath 112A is also retracted since it is coupled to collet 446. Retraction of sheath 112A initiates deployment of the stent.

Figure 5A:
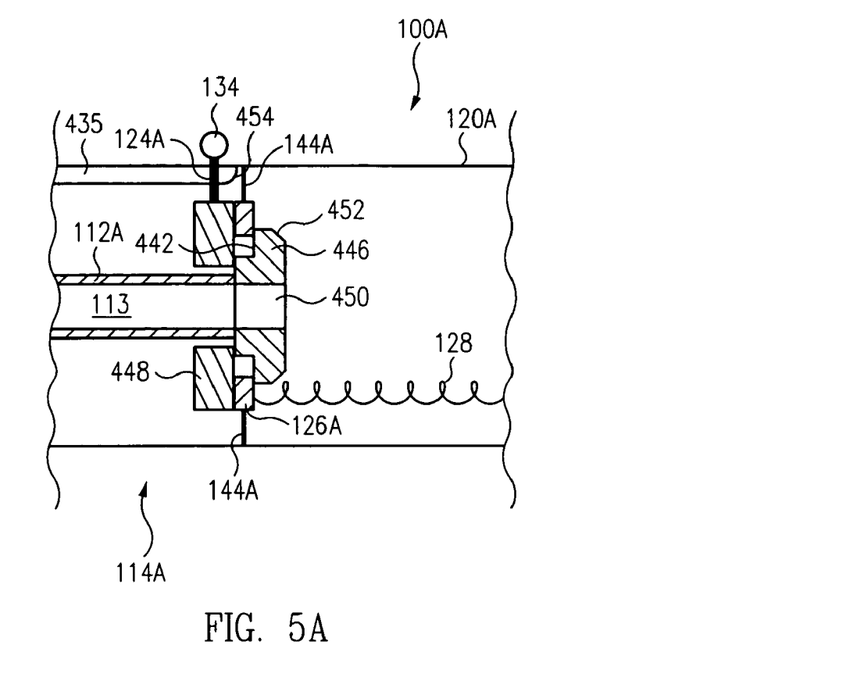
FIGS. 5A and 6 are modified partial cross-section views of the stent delivery system of FIG. 4 at further stages during deployment of the stent.

FIG. 5A is a modified partial cross-section view of stent delivery system 100A of FIG. 4 at a further stage during deployment of the stent.

As a result of retraction of slider movement mechanism 124A, collet 446 contacts and becomes connected to engagement plate 126A as shown in FIG. 5. More particularly, tapered surface 452 of collet 446 contacts engagement plate 126A allowing collet 446 to be squeezed through engagement plate 126A. Once lip 442 of collet 446 completely passed through engagement plate 126A, collet 446 snaps around engagement plate 126A thus connecting collet 446 to engagement plate 126A as shown in FIG. 5A.

Engagement plate 126A is coupled to housing 120A by at least one breakaway 144A as discussed above. Breakaways 144A have a strength sufficient to prevent disengagement of engagement plate 126A from housing 120A during coupling of collet 446 to engagement plate 126A as discussed above. However, after engagement of collet 446 to engagement plate 126A, additional force applied during the manual retraction of slider movement mechanism 124A causes breakaways 144A to release engagement plate 126A from housing 120A as discussed further below in reference to FIG. 6. More particularly, additional force applied during the manual retraction of slider movement mechanism 124A causes collar 448 to press against engagement plate 126A. This causes breakaways 144A to release engagement plate 126A from housing 120A.

Figure 5B:
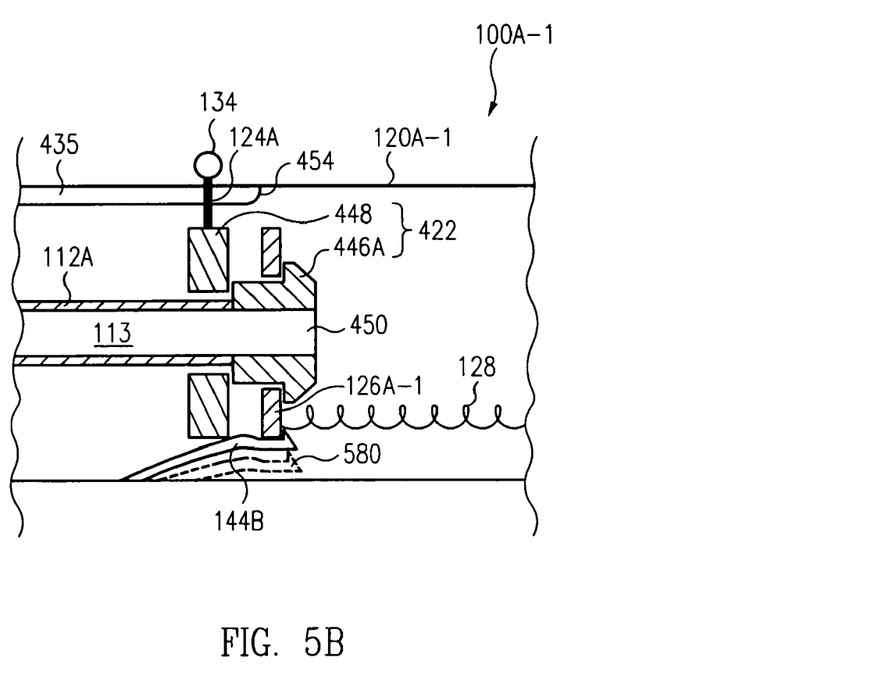
FIG. 5B is a modified partial cross-section view of a stent delivery system during release of an engagement plate.

FIG. 5B is a modified partial cross-sectional view of a stent delivery system 100A-1 during release of an engagement plate 126A-1. As shown in FIG. 5B, a collet 446A contacts and becomes connected to engagement plate 126A-1 in a manner similar to that discussed above. Further, engagement plate 126A-1 is coupled to a housing 120A-1 by at least one breakaway 144B. Breakaway 144B is a mechanism that disengages engagement plate 126A-1 from housing 120A-1 when slider movement mechanism 124A reaches a certain point in travel.

More particularly, breakaway 144B is an arm that flexes and/or pivots as collar 448 presses against (outwards) on breakaway 144B. Due to this flexing/pivoting, breakaway 144B moves to a second position 580 as indicated by the dashed line and releases engagement plate 126A-1 from housing 120A-1 in a manner similar to that discussed below with reference to FIG. 6.

Figure 6:
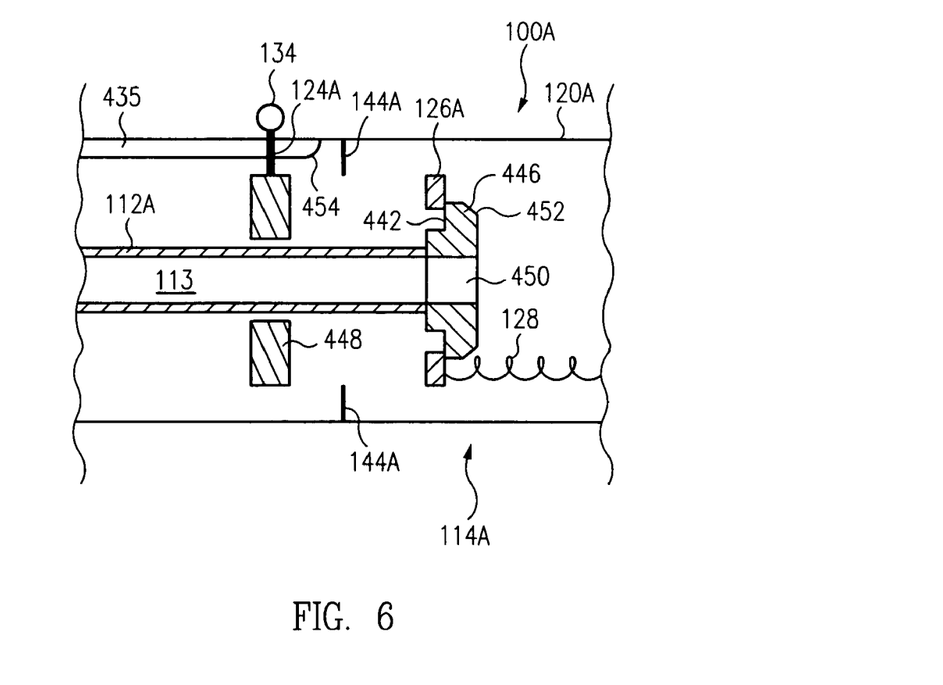

FIG. 6 is a modified partial cross-section view of stent delivery system 100A of FIG. 5A at a further stage during deployment of the stent.

Referring now to FIGS. 5A and 6 together, upon release by breakaways 144A, spring 128 pulls engagement plate 126A towards the anchor plate, i.e., automatically retracts engagement plate 126A. Since collet 446 and sheath 112A are connected to engagement plate 126A, collet 446 and sheath 112A are also pulled towards the anchor plate. This results in retraction of sheath 112A from the stent, which self-expands to become fully deployed within the parent vessel in a manner similar to that shown in FIG. 3.

Slider movement mechanism slot 435 does not extend across the entire length of delivery handle 114A but ends near breakaways 144A. Accordingly, slider movement mechanism 124A contacts the end 454 of slider movement mechanism slot 435. This prevents further motion of slider movement mechanism 124A and collar 448. However, since collar 448 is slidably coupled to sheath 112A, sheath 112A slides through collar 448 as shown in FIG. 6.

To control the speed of automatic retraction of the sheath by the spring, the delivery handle is provided with a braking mechanism, also called a speed-governing mechanism, as discussed below with reference to FIGS. 7, 8, 9, and 10.

Figure 7:
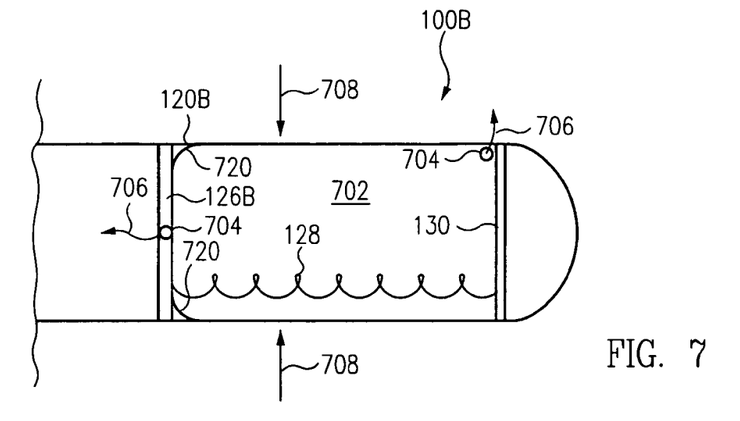
FIGS. 7, 8 and 9 are modified partial cross-section views of other stent delivery systems.

FIG. 7 is a modified partial cross-section view of a stent delivery system 100B in another embodiment according to the present invention. For simplicity, only housing 120B, anchor plate 130, spring 128, and an engagement plate 126B are illustrated.

Engagement plate 126B forms an air seal with housing 120B. More particularly, engagement plate 126B and housing 120B define a handle volume 702. As spring 128 moves engagement plate 126B towards anchor plate 130, handle volume 702 is reduced. By controlling the rate of air leakage from handle volume 702, the speed of travel of engagement plate 126B is controlled. The greater the rate of air leakage from handle volume 702, the greater the speed of travel of engagement plate 126B and vice versa.

To control the rate of air leakage from handle volume 702, housing 120B and/or engagement plate 126B is provided with one or more vent apertures 704, through which air is vented from handle volume 702 as illustrated by the arrows 706. By forming vent apertures 704 with the appropriate diameter, the speed at which engagement plate 126B travels is controlled. In the above manner, a pneumatic (air baffle) mechanism is used to slow the automatic deployment of the stent to reduce jumping, catheter recoil and alarm to the physician. As another example, by forming an imperfect seal between engagement plate 126B and housing 120B, the speed at which engagement plate 126B travels is controlled.

In yet another example, friction pads 720, sometimes called brake pads, are flexible members coupled to engagement plate 126B that press outwards on housing 120B thus controlling the speed at which engagement plate 126B travels.

Further, by squeezing housing 120B as indicated by arrows 708, e.g., with the hand of the physician, the friction between engagement plate 126B/friction pads 720 and housing 120B is increased thus slowing or stopping the speed at which engagement plate 126B travels.

Figure 8:
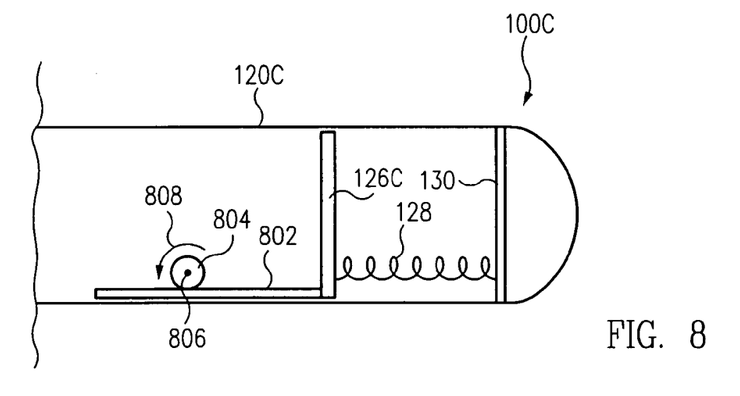

FIG. 8 is a modified partial cross-section view of a stent delivery system 100C in another embodiment according to the present invention. For simplicity, only housing 120C, anchor plate 130, spring 128, an engagement plate 126C, a brake plate 802, a brake wheel 804, and an axle 806 are illustrated. Brake plate 802 extends longitudinally, i.e., distally, from engagement plate 126C. Brake wheel 804 is engaged, e.g., with friction, to brake plate 802.

Brake wheel 804 is mounted on an axle 806 coupled to housing 120C. As engagement plate 126C moves towards anchor plate 130, brake plate 802 is pulled past brake wheel 804. This causes brake wheel 804 to rotate around axle 806 as indicated by arrow 808. Illustratively, friction between brake wheel 804 and axle 806, sometimes called a frictional mechanism, slows the rotation of brake wheel 804 and thus the speed of travel of engagement plate 126C. As another illustration, axle 806 is connected to a flywheel, e.g., a kinetic mechanism, which slows the rotation of brake wheel 804 as discussed in greater detail below with reference to FIG. 10.

Figure 9:
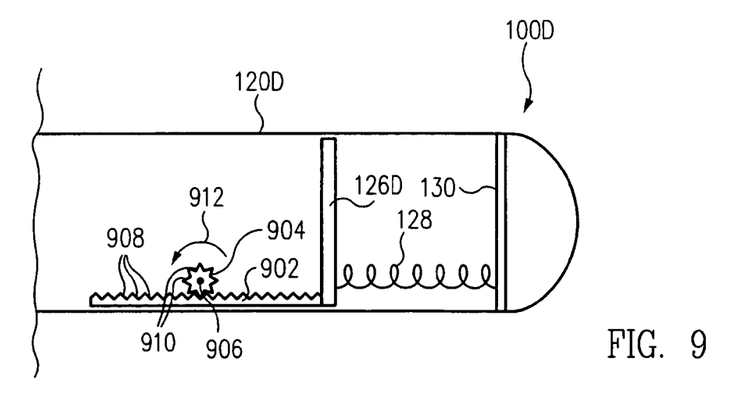

FIG. 9 is a modified partial cross-section view of a stent delivery system 100D in another embodiment according to the present invention. For simplicity, only housing 120D, anchor plate 130, spring 128, an engagement plate 126D, a brake plate 902, a brake wheel 904, and axle 906 are illustrated. Brake plate 902 extends longitudinally, i.e., distally, from engagement plate 126D. Brake wheel 904 is engaged to brake plate 902. More particularly, brake plate 902 includes a plurality of teeth 908. Brake wheel 904 also includes teeth 910 engaged with teeth 908 in a rack and pinion arrangement.

Brake wheel 904 is mounted on axle 906 coupled to housing 120D. As engagement plate 126D moves towards anchor plate 130, brake plate 902 is pulled past brake wheel 904. This causes brake wheel 904 to rotate around axle 906 as indicated by arrow 912. Illustratively, friction between brake wheel 904 and axle 906 slows the rotation of brake wheel 904 and thus slows the speed of travel of engagement plate 126D. As another illustration, axle 906 is connected to a flywheel, which slows the rotation of brake wheel 904 as discussed in greater detail below with reference to FIG. 10.

Figure 10:
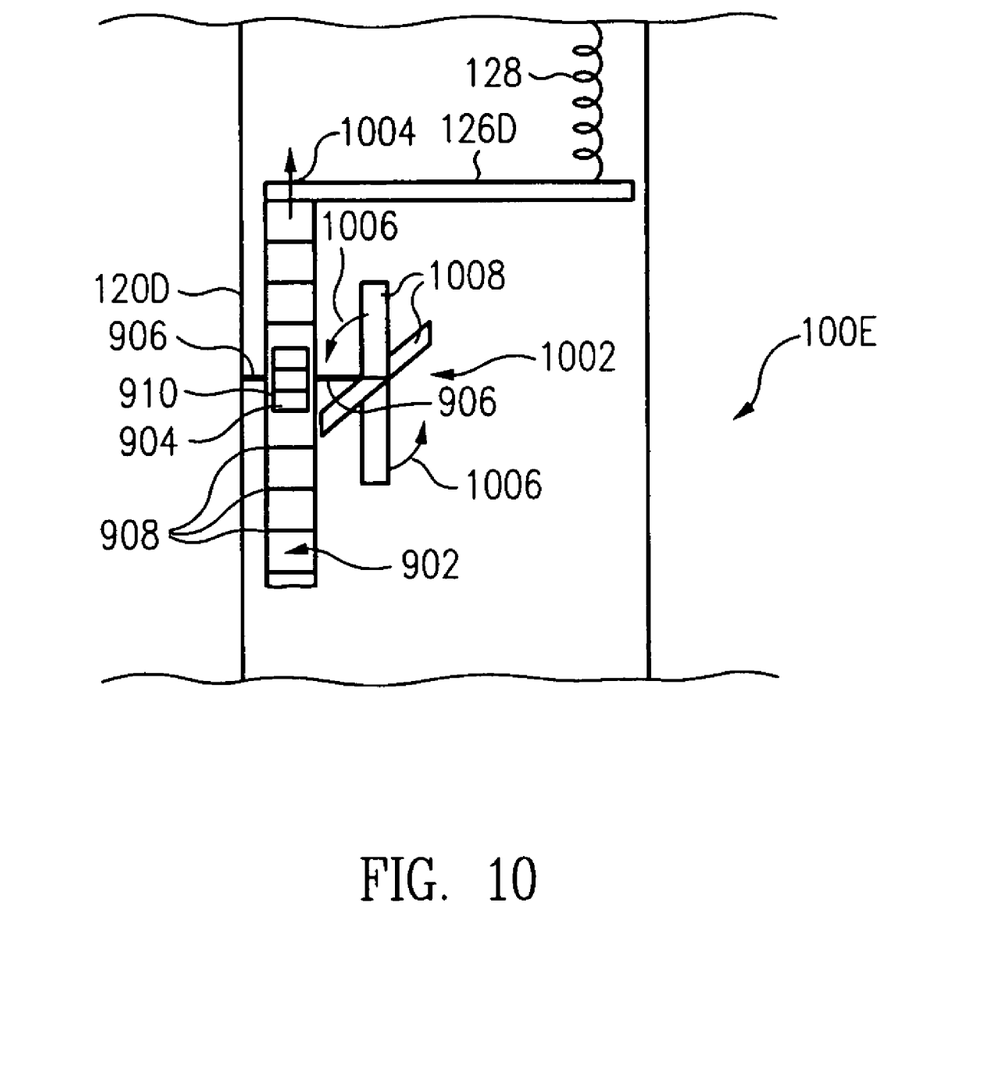
FIG. 10 is a modified partial top cross-section view of yet another stent delivery system.

FIG. 10 is a modified partial top cross-section view of a stent delivery system 100E in another embodiment according to the present invention. Stent delivery system 100E is similar to stent delivery system 100D of FIG. 9 and only the significant differences are discussed below.

Referring now to FIG. 10, stent delivery system 100E includes a flywheel 1002 mounted on axle 906. As brake wheel 904 and axle 906 rotate due to motion of brake plate 902 as indicated by arrow 1004, flywheel 1002 is spun as indicated by the arrows 1006. Illustratively, flywheel 1002 includes paddles 1008, e.g., is a paddlewheel, and friction of air on paddles 1008 slows the rotation of flywheel 1002 and, in turn, engagement plate 126D.

Figure 11:
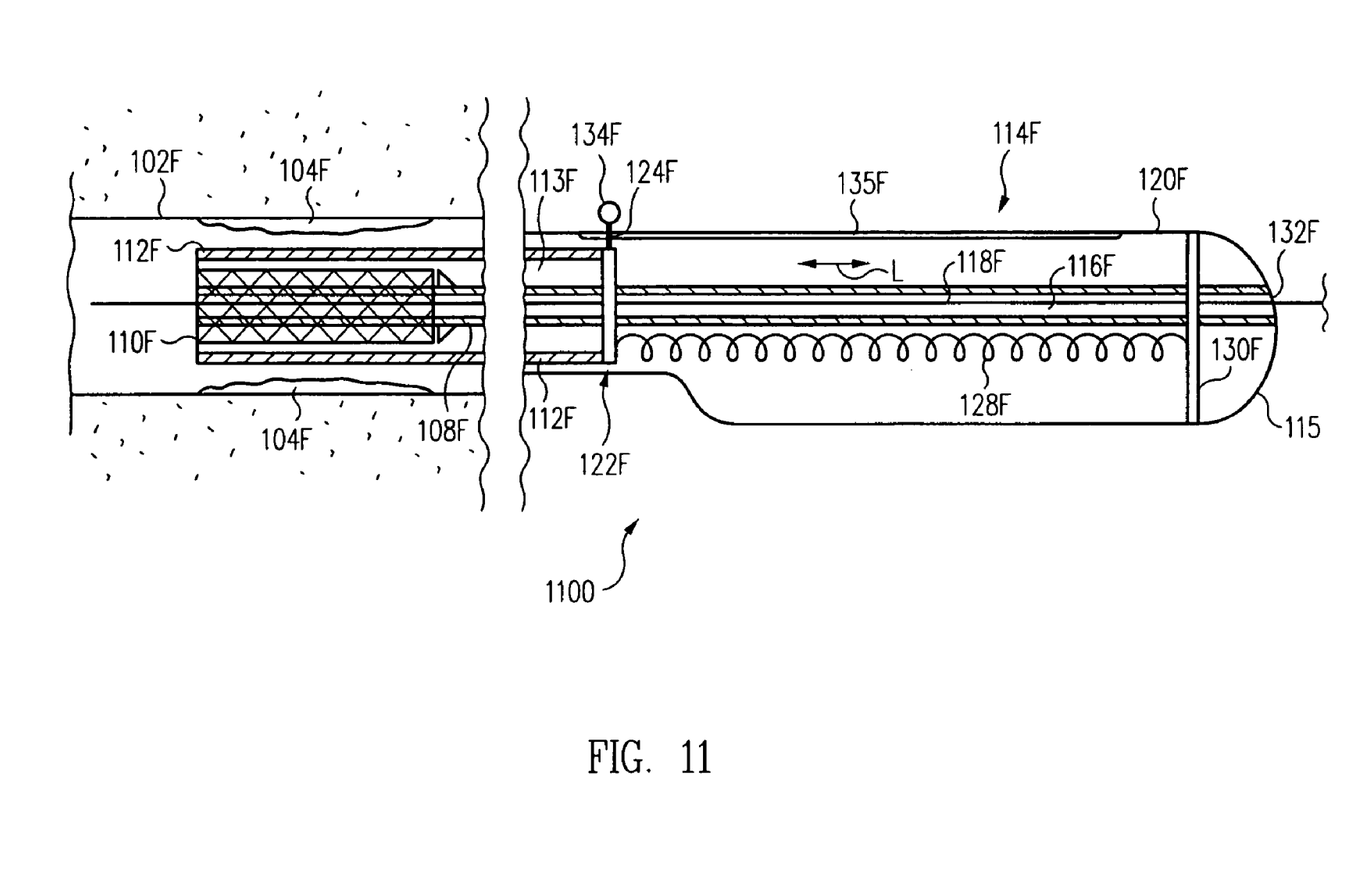
FIGS. 11 and 12 are modified partial cross-section view of other stent delivery systems.

FIG. 11 is a modified partial cross-section view of a stent delivery system 1100 within a parent vessel 102F of a patient adjacent to an occlusion 104F. Referring now to FIG. 11, delivery system 1100 includes an inner member 108F, a stent 110F, a sheath 112F, and a delivery handle 114F.

In accordance with this embodiment, inner member 108F, sometimes called a pushrod, is a hollow tubular member and includes a lumen 116F, e.g., a guidewire lumen, through which a guidewire 118F extends.

Stent 110F is placed over and mounted around inner member 108F. Stent 110F is radially constrained by sheath 112F. More particularly, prior to deployment, stent 110F is located within sheath 112F. Sheath 112F extends into and is coupled to delivery handle 114F as discussed further below. Sheath 112F includes a lumen 113F through which inner member 108F and guidewire 118F extend.

Delivery handle 114F includes a housing 120F, a slider 122F, a slider movement mechanism 124F, a spring 128F, and an anchor plate 130F. Inner member 108F extends through delivery handle 114F to a guidewire port 132F of housing 120F. More particularly, slider 122F and anchor plate 130F include apertures through which inner member 108F passes.

Slider 122F is coupled to slider movement mechanism 124F, which is slidably coupled to housing 120F. Slider movement mechanism 124F, sometimes called a thumb slider, includes an actuation button 134F. Slider movement mechanism 124F extends from inside housing 120F through a slider movement mechanism slot 135F of housing 120F.

Sheath 112F is coupled to or integral with slider 122F. Depression of actuation button 134F (or circumferential rotation) disengages slider movement mechanism 124F from housing 120F. This allows slider movement mechanism 124F, and thus slider 122F and sheath 112F, to be moved longitudinally along a longitudinal axis L of delivery handle 114F.

Anchor plate 130F is fixed to or integral with housing 120F. Slider 122F is coupled to anchor plate 130F by spring 128F. Spring 128F is in tension and is a source of stored energy. Although spring 128F is set forth, other sources of stored energy can be used. Further, it is understood that the figures are not to scale and the ratio of the expanded length to the compressed length of spring 128F can be other than that illustrated.

As discussed above, slider 122F is coupled to housing 120F by slider movement mechanism 124F. After disengagement of slider 122F from housing 120F, e.g., by circumferential rotation of actuation button 134F, spring 128F moves (pulls) slider 122F towards anchor plate 130F, i.e., automatically retracts slider 122F. Since sheath 112F is connected to slider 122F, sheath 112F is also pulled towards anchor plate 130F.

This results in the initial manual deployment of stent 110F by the physician being spring assisted. Following the initial manual deployment and upon release of actuation button 134F by the physician, sheath 112F is automatically retracted from the remaining length of stent 110F by spring 128F, which causes stent 110F to self-expand and become fully deployed within parent vessel 102F.

Use of delivery handle 114F is particularly well suited for use when stent 110F is long. More particularly, the initial deployment of stent 110F is performed by the physician manually with the assistance of spring 128F. This provides the physician with control of the initial deployment of stent 110F. Further, once stent 110F is securely engaged within parent vessel 102F, the remaining deployment over the remaining length of stent 110F is performed automatically by retraction of sheath 112F by spring 128F as discussed above. Since the physician simply initiates deployment, the deployment of stent 110F is readily performed using only a single hand of the physician. Accordingly, use of delivery handle 114F allows deployment of relatively long stents in a very simple manner.

In one example, stent 110F is entirely deployed automatically by spring 128F. In this example, the physician simply disengages slider 122F from housing 120F, e.g., circumferentially rotates actuation button 134F, and releases actuation button 134F. Upon release of actuation button 134F, spring 128F automatically retracts slider 122F. Accordingly, sheath 112F is automatically retracted from the entire length of stent 110F by spring 128F, which causes stent 110F to self-expand and become fully deployed within parent vessel 102F.

Figure 12:
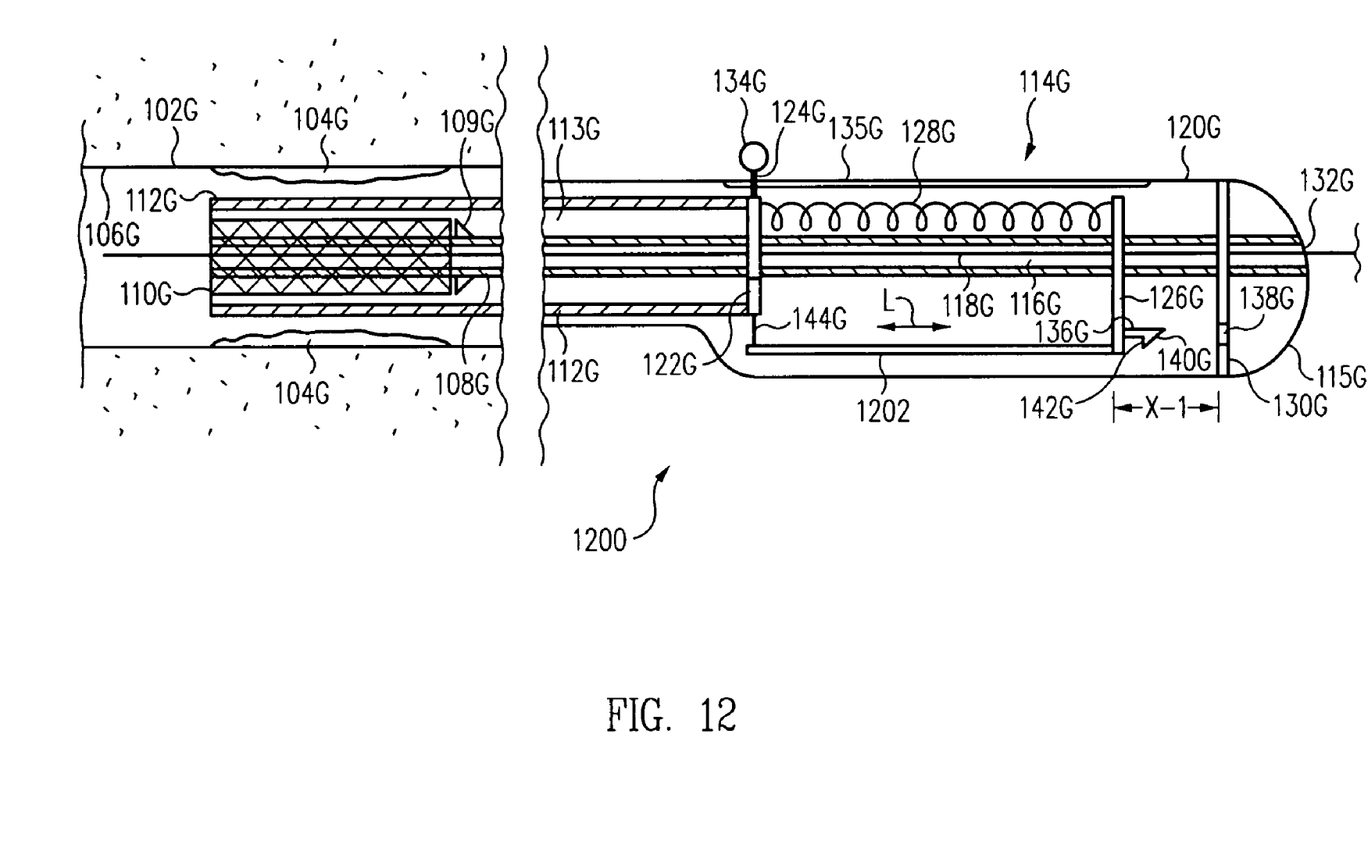

FIG. 12 is a modified partial cross-section view of a stent delivery system 1200 within a parent vessel 102G of a patient adjacent to an occlusion 104G. Delivery system 1200 includes an inner member 108G, a stent 110G, a sheath 112G, and a delivery handle 114G.

In accordance with this embodiment, inner member 108G, sometimes called a pushrod, is a hollow tubular member and includes a lumen 116G, e.g., a guidewire lumen, through which a guidewire 118G extends.

Stent 110G is placed over and mounted around inner member 108G. Stent 110G is radially constrained by sheath 112G. More particularly, prior to deployment, stent 110G is located within sheath 112G. Sheath 112G extends into and is coupled to delivery handle 114G as discussed further below. Sheath 112G includes a lumen 113G through which inner member 108G and guidewire 118G extend.

Delivery handle 114G includes a housing 120G, a slider 122G, a slider movement mechanism 124G, an engagement plate 126G, an engagement plate support member 1202, a spring 128G, and an anchor plate 130G. Inner member 108G extends through delivery handle 114G to a guidewire port 132G of housing 120G. More particularly, slider 122G, engagement plate 126G, and anchor plate 130G include apertures through which inner member 108G passes.

Slider 122G is coupled to slider movement mechanism 124G, which is slidably coupled to housing 120G. Slider movement mechanism 124G, sometimes called a thumb slider, includes an actuation button 134G. Slider movement mechanism 124G extends from inside housing 120G through a slider movement mechanism slot 135G of housing 120G.

Slider 122G is coupled to engagement plate support member 1202 by at least one breakaway 144G of delivery handle 114G. Engagement plate support member 1202 is fixed to or integral with engagement plate 126G. Engagement plate support member 1202 is a rigid member which holds spring 128G open and prevents slider 122G from moving relative to engagement plate 126G during initial deployment.

Engagement plate 126G is coupled to slider 122G by spring 128G. Spring 128G is in tension and is a source of stored energy. Although spring 128G is set forth, other sources of stored energy can be used. Further, it is understood that the figures are not to scale and the ratio of the expanded length to the compressed length of spring 128G can be other than that illustrated.

Breakaway 144G has a strength sufficient to prevent disengagement of slider 122G from engagement plate support member 1202 during coupling of engagement plate 126G to anchor plate 130G and from the tension in spring 128G as discussed below. However, after engagement of engagement plate 126G to anchor plate 130G, additional force applied during the manual retraction of slider movement mechanism 124G causes breakaway 144G to release slider 122G from engagement plate support member 1202 as also discussed further below.

In one example, breakaway 144G is a thin strip of molding between slider 122G and engagement plate support member 1202 and breaks or snaps to release slider 122G from engagement plate support member 1202. In another example, breakaway 144G is a mechanism that disengages slider 122G from engagement plate support member 1202 when slider movement mechanism 124G reaches a certain point in travel in a manner similar to that discussed above with reference to FIG. 5B.

Sheath 112G is coupled to or integral with slider 122G. Depression of actuation button 134G (or circumferential rotation) disengages slider movement mechanism 124G from housing 120G. This allows slider movement mechanism 124G, and thus sheath 112G, slider 122G, engagement plate support member 1202, breakaway 144G, spring 128G and engagement plate 126G to be moved longitudinally along a longitudinal axis L of delivery handle 114G.

Prior to retraction of sheath 112G, a longitudinal manual pull distance X–1 exists between engagement plate 126G and anchor plate 130G. Engagement plate 126G and anchor plate 130G include means for connecting engagement plate 126G to anchor plate 130G. More particularly, engagement plate 126G includes one or more locking protrusions 136G, sometimes called a tab or hook, extending from engagement plate 126G towards anchor plate 130G. Anchor plate 130G includes one or more locking apertures 138G corresponding to and aligned with locking protrusion(s) 136G.

During initial deployment, engagement plate 126G is retracted towards anchor plate 130G such that locking protrusion 136G passes through corresponding locking aperture 138G and snaps to connect engagement plate 126G to anchor plate 130G.

Further, during initial deployment, the first few segments of stent 110G are uncovered by sheath 112G and exposed. As a result, the first few segments of stent 110G self-expand into occlusion 104G and inner vessel wall 106G of parent vessel 102G thus providing a force opening that part of parent vessel 102G and engaging stent 110G to inner vessel wall 106G. Inner member 108G includes a stop 109G or other holding member, which prevents movement of stent 110G during retraction of sheath 112G.

These first few segments of stent 110G are deployed manually by the physician. This allows the physician to carefully deploy the first few segments of stent 110G to achieve the desired positioning of stent 110G within parent vessel 102G and occlusion 104G. Further, by manually deploying the first few segments of stent 110G, the physician is in complete control of the initial deployment further facilitating the desired positioning of stent 110G within parent vessel 102G and occlusion 104G.

After slider movement mechanism 124G, sheath 112G, slider 122G, engagement plate support member 1202, breakaway 144G, spring 128G and engagement plate 126G are retracted, i.e., moved manual pull distance X–1, engagement plate 126G contacts and connects to anchor plate 130G.

More particularly, locking protrusion 136G includes a tapered surface 140G, i.e., a surface angled with respect to longitudinal axis L of delivery handle 114G. Tapered surface 140G contact the side of locking aperture 138G. Locking protrusion 136G is thus bent as slider 122G is retracted. Locking protrusion 136G further includes a lip 142G, e.g., a surface perpendicular to longitudinal axis L of delivery handle 114G. Once lip 142G of locking protrusion 136G completely passes through locking aperture 138G, locking protrusion 136G snaps around anchor plate 130G thus connecting engagement plate 126G to anchor plate 130G.

To complete deployment of stent 110G, upon release by breakaway 144G and disengagement of slider 122G from engagement plate support member 1202, spring 128G moves (pulls) slider 122G towards anchor plate 130G, i.e., automatically retracts slider 122G. Since sheath 112G is connected to slider 122G, sheath 112G is also pulled towards anchor plate 130G. This results in automatic retraction of sheath 112G from stent 110G, which self-expands to become fully deployed within parent vessel 102G.

Use of delivery handle 114G is particularly well suited for use when stent 110G is long. More particularly, the initial deployment of stent 110G is performed by the physician manually. This provides the physician with complete control of the initial deployment of stent 110G. Further, once stent 110G is securely engaged within parent vessel 102G, the remaining deployment over the remaining length of stent 110G is performed automatically by retraction of sheath 112G by spring 128G as discussed above. Since the physician simply moves the slider movement mechanism 124G over the relatively short manual pull distance X−1, the deployment of stent 110G is readily performed using only a single hand of the physician. Accordingly, use of delivery handle 114G allows deployment of relatively long stents in a very simple manner.

This disclosure provides exemplary embodiments of the present invention. The scope of the present invention is not limited by these exemplary embodiments. Numerous variations, whether explicitly provided for by the specification or implied by the specification or not, such as variations in structure, dimension, type of material and manufacturing process may be implemented by one of skill in the art in view of this disclosure.

What is claimed is:

1. A delivery system comprising:
   a housing;
   a sheath;
   a slider coupled to said sheath, said slider being located within said housing;
   an engagement plate located within said housing, said engagement plate coupled to said housing by at least one breakaway, wherein said at least one breakaway breaks to disengage said engagement plate from said housing, wherein retraction of said slider causes said slider to directly contact and connect to said engagement plate; and
   a source of stored energy coupled to said engagement plate.

2. The delivery system of claim 1 wherein said slider comprises a collet and a collar.

3. The delivery system of claim 2 wherein said collet comprises a tapered surface for facilitating coupling of said collet to said engagement plate.

4. The delivery system of claim 2 wherein said collar is an annulus slidably mounted around said sheath.

5. The delivery system of claim 2 wherein said collet is coupled to said engagement plate.

6. The delivery system of claim 2 wherein said engagement plate is an annular shaped member.

7. The delivery system of claim 2 wherein said collet includes an aperture aligned with a lumen of said sheath.

8. The delivery system of claim 1 wherein a slider movement mechanism slot of said housing ends near said at least one breakaway.

9. The delivery system of claim 1 wherein said at least one breakaway is a mechanism that disengages said engagement plate from said housing.

10. The delivery system of claim 1 further comprising a braking mechanism coupled to said engagement plate.

11. The delivery system of claim 10 wherein said braking mechanism is selected from the group consisting of a frictional mechanism, a pneumatic mechanism and a kinetic mechanism.

12. The delivery system of claim 10 wherein said braking mechanism comprises an air seal between said engagement plate and said housing.

13. The delivery system of claim 12 further comprising one or more vent apertures allowing air to escape.

14. The delivery system of claim 10 wherein said braking mechanism comprises a brake plate coupled to said engagement plate and a brake wheel coupled to said housing, said brake wheel engaged with said brake plate.

15. The delivery system of claim 14 wherein said brake plate comprises teeth coupled to teeth of said brake wheel in a rack and pinion arrangement.

16. The delivery system of claim 14 further comprising a flywheel coupled to said brake wheel.

17. The delivery system of claim 16 wherein said flywheel comprises paddles.

18. The delivery system of claim 10 wherein said braking mechanism comprises friction pads coupled to said engagement plate, said friction pads being flexible members that press against said housing.

19. The delivery system of claim 1 wherein said source of stored energy comprises a spring.

20. The delivery system of claim 19 further comprising an anchor plate coupled to said spring.

21. The delivery system of claim 1 further comprising a stent constrained by said sheath.

22. The delivery system of claim 21 further comprising an inner member, said stent being positioned around said inner member.

23. The delivery system of claim 1 further comprising a slider movement mechanism coupled to said slider, said slider movement mechanism extending from inside said housing through a slider movement mechanism slot of said housing.

24. The delivery system of claim 1 further comprising means for connecting said slider to said engagement plate.

25. The delivery system of claim 1 wherein said slider comprises locking protrusions and said engagement plate comprises locking apertures aligned with said locking protrusions.

26. The delivery system of claim 1 wherein said at least one breakaway comprises a thin strip of molding between said engagement plate and said housing.

27. A delivery system comprising:
   a housing;
   a sheath;
   a slider coupled to said sheath, said slider being located within said housing;
   an engagement plate located within said housing, said engagement plate coupled to said housing by at least one breakaway, wherein said at least one breakaway breaks to disengage said engagement plate from said housing, wherein said slider and said engagement plate comprise means for connecting said slider to said engagement plate upon contact of said slider with said engagement plate;
   an anchor plate coupled to said housing; and
   a source of stored energy directly coupled to said engagement plate and said anchor plate.

* * * * *

UNITED STATES PATENT AND TRADEMARK OFFICE
CERTIFICATE OF CORRECTION

PATENT NO. : 7,635,382 B2
APPLICATION NO. : 10/691747
DATED : December 22, 2009
INVENTOR(S) : Jack D. Pryor It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1179 days.

Signed and Sealed this

Twenty-first Day of December, 2010

David J. Kappos
*Director of the United States Patent and Trademark Office*